United States Patent [19]

Kraft et al.

[11] Patent Number: 4,488,812
[45] Date of Patent: Dec. 18, 1984

[54] PHOTOMETRIC APPARATUS

[75] Inventors: Thomas L. Kraft; Howard A. Vick; James W. Meador, all of Houston, Tex.

[73] Assignee: American Home Products Corporation, New York, N.Y.

[21] Appl. No.: 268,205

[22] Filed: May 29, 1981

Related U.S. Application Data

[62] Division of Ser. No. 041,475, May 22, 1979, Pat. No. 4,291,983.

[51] Int. Cl.³ .................... G01N 21/00; G01J 1/42
[52] U.S. Cl. ................... 356/338; 250/564; 356/226; 356/228
[58] Field of Search .............. 356/338–343, 356/434–437, 438–444, 70, 226, 228; 250/564, 573, 252.1; 324/74; 364/571; 73/1 G

[56] References Cited

U.S. PATENT DOCUMENTS

| | | | |
|---|---|---|---|
| 2,769,365 | 11/1956 | Loeschcke et al. | 356/442 |
| 3,185,975 | 5/1965 | Kompelien | 356/338 |
| 3,361,030 | 1/1968 | Goldberg | 250/574 X |
| 3,549,893 | 12/1970 | Gibbs | 250/577 |
| 3,873,206 | 3/1975 | Wilcock | 356/338 |
| 3,990,851 | 11/1976 | Gross et al. | 356/338 |
| 4,027,973 | 6/1977 | Kaye | 356/338 |
| 4,037,965 | 7/1977 | Weiss | 356/338 |
| 4,072,421 | 2/1978 | Coyne et al. | 356/39 |
| 4,077,724 | 3/1978 | Briggs | 356/442 |
| 4,176,953 | 12/1979 | Bartoov et al. | 356/436 |

OTHER PUBLICATIONS

Schimizu, K. and Ishimaru, A., "Scattering Pattern Analysis of Bacteria", Optical Engineering, vol. 17, No. 2, Mar.–Apr. 1978, pp. 129–134.

Primary Examiner—Bruce Y. Arnold
Attorney, Agent, or Firm—Edward M. Blocker

[57] ABSTRACT

A photometric analyzer and method are disclosed for analyzing particle containing samples. More particularly, a nephelometric apparatus and method are disclosed for analyzing baceteria samples. In the disclosed embodiment, the bacteria count of a bacteria sample is determined by photometrically comparing the sample to another sample having a known particle or bacteria concentration. Thus, in accordance with the invention, samples having a known bacteria count may be quickly and easily obtained from a "go" "no-go" test. The bacteria samples obtained according to the invention may be used as standardized bacteria concentrations for conducting Kirby-Bauer dilution tests.

6 Claims, 6 Drawing Figures

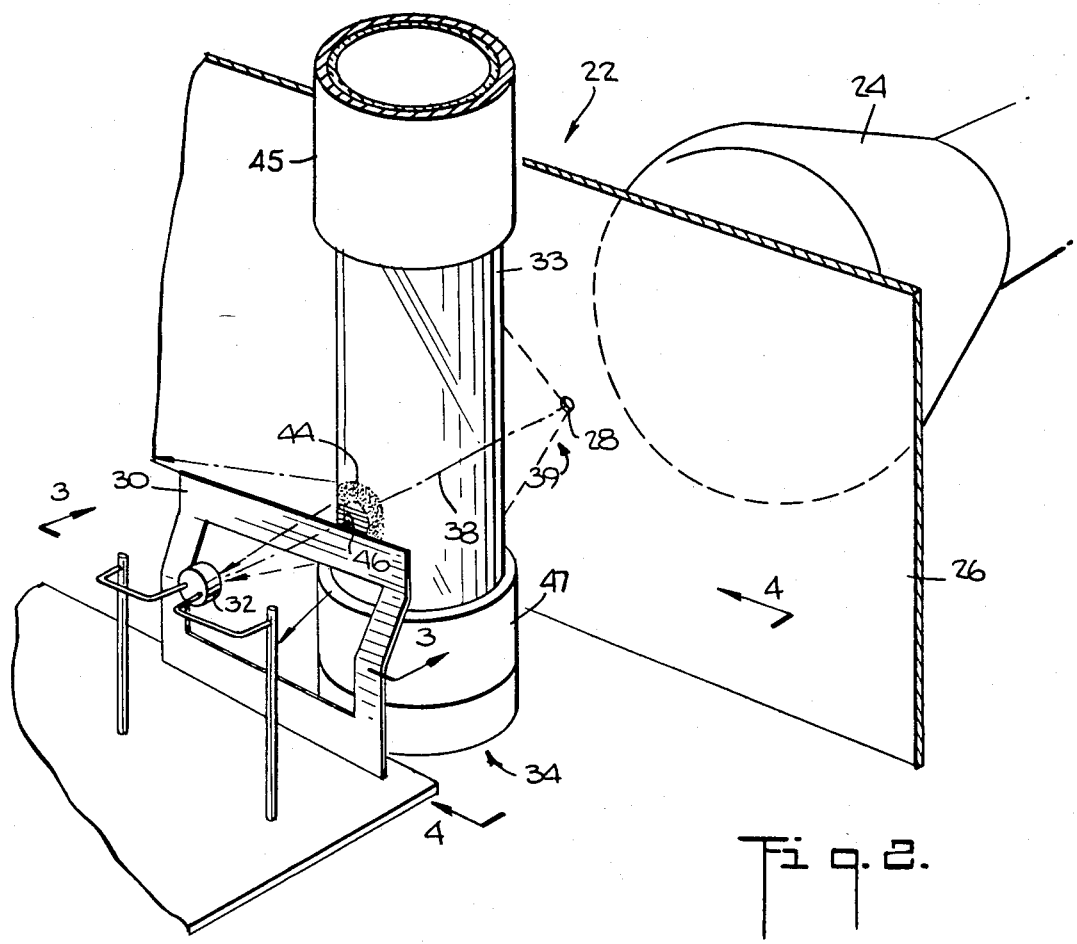
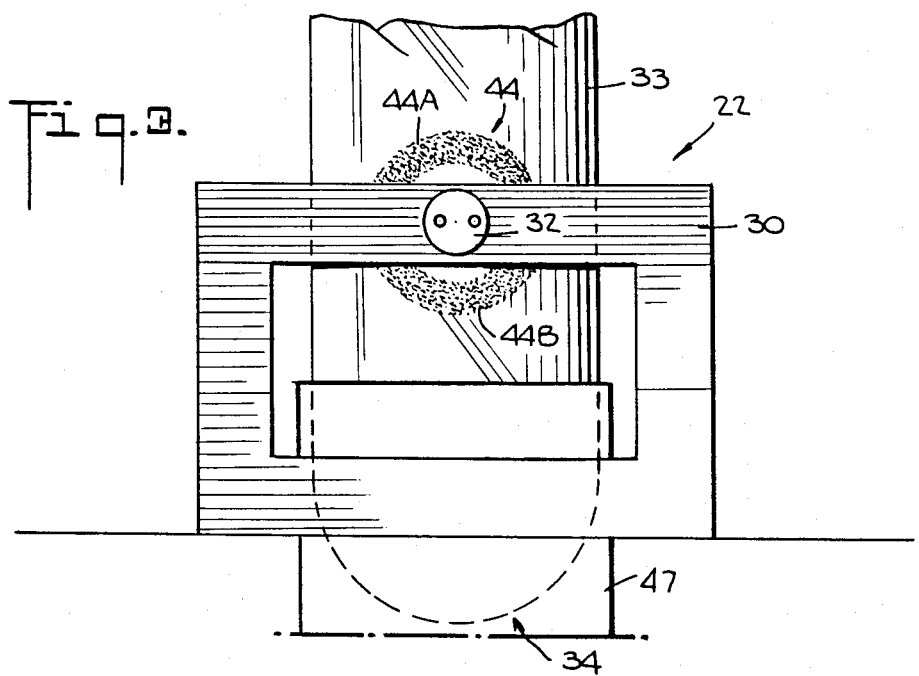

4,488,812

PHOTOMETRIC APPARATUS

This is a division of application Ser. No. 41,475, filed May 22, 1979, which has issued as U.S. Pat. No. 4,291,983.

BACKGROUND OF THE INVENTION

The present invention relates to the photometric analysis of samples, and more particularly to the nephelometric analysis of bacteria samples.

DESCRIPTION OF THE PRIOR ART

Photometric analysis apparatus and methods are known in which light is projected towards the sample to be analyzed and the light emerging from predetermined regions of the sample is detected by photoelectric means while light emerging from the sample in regions other than the predetermined regions is prevented from reaching the photoelectric means.

In Loeschcke et al. U.S. Pat. No. 2,769,365, two photoelectric cells are provided, one for receiving the light emerging from a predetermined region of the sample corresponding to light diffracted and diffused by the sample and the other for receiving undiffracted and undiffused light. A lens is used to collect the light projected by the light source and transmit the collected light towards the sample. Both cells are coupled to a galvanometer which reads a null when both cells are receiving the same amount of light. The undiffracted and undiffused light reaching the other photoelectric cell is adjusted to obtain a null reading on the galvanometer. The adjustment is calibrated to read the number of particles in the sample.

In Coyne et al. U.S. Pat. No. 4,072,421, lenses are used to focus light from a light source at an optical interaction station through which particles are passed and to focus the light scattered by certain particles which are to be counted on a photodetector. The unscattered light passing through the optical interaction station and the light from other particles is prevented from reaching the photodetector by a light stop disposed on an optical axis extending between the photodetector and the light source. A particle of the concerned type is counted each time scattered light is detected by the photodetector.

Kompelin U.S. Pat. No. 3,185,975 discloses a photoelectric smoke detector in which light from a light source is projected across a relatively large surface area and any light reflected by particles which lie in an annular space in the large surface area are detected A light block is interposed between the light source and a photocell on an optical axis therebetween to prevent light, both reflected and direct, which is in a central region on the side of the light block facing the light source from reaching the photocell.

Gibbs U.S. Pat. No. 3,549,893 discloses a photoelectric electric liquid level sensor. Light is projected towards a chamber in which the liquid level is to be sensed. A light responsive cell is disposed on the other side of the chamber and a light baffle is disposed between the cell and the chamber. Light passing through an empty chamber diverges and is prevented from reaching the cell by the baffle because the cell is disposed to be in an umbra produced by the baffle. When a liquid is present in the chamber, the light passing through the liquid is converged and the light in a penumbra reaches the cell.

In performing Kirby-Bauer bacteria sensitivity tests, various drugs are introduced into a bacteria sample and the reactions of the bacteria to the drugs are tested. In order to run the tests, the bacteria sample is standardized to have a predetermined bacteria count.

SUMMARY OF THE INVENTION

It is an object of the present invention to provide a simple and relatively inexpensive photometric apparatus.

It is another object of the present invention to provide a photometric apparatus and method for comparing an unknown sample to a known sample.

It is still another object of the present invention to provide a simple and inexpensive nephelometric apparatus and method for analyzing samples.

It is also an object of the present invention to provide a nephelometric apparatus and method for comparing an unknown to a known sample.

It is a further object of the present invention to provide an apparatus and method for photometrically comparing an unknown sample to a known sample on a "go", "no-go" test basis.

In accordance with the invention, nephelometric apparatus and a method are provided for analyzing a fluid sample of particulate material. A beam of light is projected about an optical axis towards the sample, the light diverging from the optical axis. Light emerging from a predetermined region in the sample is permitted to reach photoelectric means spaced from the sample while light propagating along the optical axis and in a region extending radially about the axis is prevented from reaching the photoelectric means. Transmission of the direct image of a light source means projecting the beam of light is also prevented from reaching the photoelectric means. Accordingly, the light reaching the photoelectric means will be proportional to the amount of light scattered through an angular range (determined with respect to the optical axis) by the particulate material in the sample. An electrical characteristic of the photoelectric means which is dependent upon the light which reaches the photoelectric means may be used to determine selected characteristics of the sample, such as the concentration of particulate material in the sample.

More specifically, a sample is photometrically analyzed according to one aspect of the invention by:

projecting a beam of light about an optical axis towards the sample, the projected light diverging from the optical axis; permitting light emerging from the sample in a predetermined region spaced from and extending radially about the optical axis to be detected at a location spaced from the sample; preventing light propagating along the optical axis and in an adjacent region extending radially about the axis from being detected at said location; and providing an indication of the count of the sample proportional to the amount of light detected. In accordance with a preferred embodiment, light propagating along the optical axis and in the adjacent region is prevented from being detected after such light emerges from the sample. This is accomplished by means disposed between the sample and photoelectric means which photoelectric means receive and detect the light in the predetermined region.

According to another aspect of the invention, an unknown sample is compared to a known sample by projecting light having given optical characteristics towards the known sample and detecting light emerging therefrom; adjusting an indication of the intensity of the light detected to provide a first reading; projecting light with the given optical characteristics towards the unknown sample and obtaining a second indication thereof; and comparing the first and second indications.

In accordance with still another aspect of the invention, nephelometer apparatus is provided for analyzing a fluid sample of particulate material disposed in a container comprising:

light source means for projecting light about an optical axis, the projected light diverging from the optical axis; photoelectric means spaced from the light source and disposed adjacent said optical axis for receiving light from the light source means, the electrical characteristics of the photoelectric means being dependent upon the intensity of light received by the photoelectric means; means for positioning the container at a predetermined location intersecting the diverging projected light and spaced apart from the light source means and the photoelectric means; first baffle means opaque to the light from the light source means disposed adjacent one of the opposite sides of the positioning means and intersecting said optical axis and extending generally radially therefrom for preventing light in a first predetermined region extending radially about the optical axis and including any direct image of the light source means from reaching the photoelectric means while permitting light emerging from the container in the positioning means in a spaced predetermined region extending radially beyond said first predetermined region to reach the photoelectric means; and indicator means coupled to said photoelectric means for proportionally indicating the intensity of the light received by the photoelectric means in accordance with the electrical characteristics of the photoelectric means.

In a preferred embodiment, the light source means comprises a light source and a second baffle means opaque to the light source disposed intermediate the positioning means and the light source, the second baffle means having an orifice therein in alignment with the optical axis. The area of the orifice is substantially smaller than the area of the light source from which the light is projected and the orifice is preferably beveled on the side thereof opposite to the light source.

In one embodiment, the first baffle means is disposed intermediate the positioning means and the photoelectric means, whereby the light in the first predetermined region and including any optical image of the light source means emerging from the container is prevented from reaching the photoelectric means. The first baffle means extends radially in one direction to prevent all light emerging along said direction from the container in the positioning means from reaching the photoelectric means while permitting light in a radial portion of the second predetermined region to reach the photoelectric means. The positioning means is disposed in the apparatus to receive a cylindrically-shaped sample container having a cylinder axis disposed transverse to the optical axis, and the first baffle means comprises an elongated member disposed transverse to the optical axis and the cylinder axis. The photoelectric means comprises a photoresistor and the indicator means comprises a meter electrically coupled with the photoresistor.

In accordance with another aspect of the invention, photometric apparatus is provided comprising: means for positioning a container holding a sample to be analyzed; a source of light disposed to one side of the positioning means for projecting light towards the positioning means to impinge on the container in the positioning means; photoelectric means disposed on a side of the positioning means opposed to said one side for receiving light emerging from the container in the positioning means, the electrical characteristics of the photoelectric means being dependent on the intensity of the light received by the photoelectric means; indicator means coupled to said photoelectric means for proportionally indicating the intensity of the light received by the photoelectric means in accordance with the electrical characteristics of the photoelectric means; first adjustment means coupled to said indicator means for adjusting the indication of the indicator means when the container contains a "zero" sample; second adjustment means coupled to said indicator means for adjusting the indication of the indicator means when the sample container contains a standard sample; whereby after the first and second adjustment means have been adjusted, a container holding an unknown sample when received in the positioning means can be calibrated against the standard sample when the indicator means has the same indication as that for the standard sample.

In accordance with a further aspect of the invention, photometric apparatus is provided comprising: a source of light for projecting light towards a sample to be analyzed; photoelectric means positioned to receive light projected by the source emerging from the sample and having electrical characteristics dependent upon the light received by the photoelectric means; DC power source means for providing DC power at an output thereof which is coupled to the photoelectric means; indicator means coupled to the photoelectric means for indicating an electrical characteristic of the photoelectric means; first adjustment means coupled between the photoelectric means and the DC power source means for adjusting the DC power provided to the photoelectric means; and second adjustment means including means for providing DC power to the indicator means at a level which is adjustable. In the preferred embodiment according to this aspect of the invention: the first adjustment means comprises a resistive voltage divider coupled between the output of the source of DC power and the photoelectric means; the photometric means comprises a photoresistor; and the second adjustment means comprises a resistive voltage divider coupled between the source of AC power and the indicator means and includes a potentiometer having its fixed terminals coupled to the source of AC power and its adjustable terminal coupled to the indicator means through the rectifier means which comprises a diode connected to provide a negative half-wave rectified voltage to the indicator means, the DC power source means providing a positive DC voltage to the first adjustment means.

Standardized concentrations of bacteria samples are used to determine the sensitivity of the bacteria to different drugs. For example, in the Kirby-Bauer dilution tests, various drugs and various concentrations thereof are introduced into a standardized bacteria sample to determine whether the bacteria is sensitive or resistant to the drug and the different concentrations thereof. In accordance with the Kirby-Bauer test, the minimum inhibitory concentration (MIC) of a drug for a particular bacteria may be determined.

Bacteria samples used in Kirby-Bauer dilution tests are standardized to have an actual bacteria count of from about $0.5 \times 10^8$ to about $5 \times 10^8$ per ml depending upon the particular bacteria. For example, for staphylococus bacteria, the standardized count is about $0.5 \times 10^8$ per ml and for pseudomonas bacteria the standardized count is about $5 \times 10^8$ per ml.

It has been found that bacteria samples having the same photometric reading taken according to the invention as a McFarland standard concentration will have an actual bacteria count of from about 1 to about $2 \times 10^8$ per ml and are suitable as standards for conducting Kirby-Bauer dilution tests. Thus, in accordance with the invention, different bacteria samples whose desired standardized concentration varies from about $0.5 \times 10^8$ to about $5 \times 10^8$ per ml, a range of ten for the different bacteria counts, may be obtained with an actual count of from about 1 to about $2 \times 10^8$ bacteria per ml, a range of 2, and may be used as standard concentrations in Kirby-Bauer dilution tests.

For example, a staphylococcus stample standardized, according to the invention will have a count of from about $1 \times 10^8$ per ml to about $2 \times 10^8$ per ml and a pseudomonas sample standardized according to the invention will also have a count of from about $1 \times 10^8$ to about $2 \times 10^8$ per ml, both relatively close to the desired counts of $0.5 \times 10^8$ per ml and $5 \times 10^8$ per ml, respectively.

According to this aspect of the invention, the bacteria count in a bacteria sample is compared to the particle count in a McFarland standard concentration by: projecting a beam of light about an optical axis towards the McFarland standard concentration in a first container at a predetermined location; detecting light emerging from the McFarland standard concentration in a predetermined annular region of the first container radially displaced from the optical axis; obtaining a reference indication proportional to the light detected emerging from the McFarland standard concentration in the predetermined annular region; projecting light in the beam and along the optical axis towards a bacteria sample in a second container which is substantially identical to the first container at the predetermined location; detecting light emerging from the bacteria sample in the predetermined annular region; obtaining another indication proportional to the light detected emerging from the bacteria sample in the predetermined annular region; and comparing the other indication to the reference indication.

In accordance with a preferred embodiment of the invention, a photometric apparatus and method are provided for standardizing a bacteria sample quickly and relatively accurately and at a low cost.

These and other aspects of the present invention will be more apparent from the following description of the preferred embodiment when considered with the accompanying drawings.

BRIEF DESCRIPTION OF THE DRAWINGS

The present invention is illustrated by way of example and not limitation in the figures of the accompanying drawings in which like numerals indicate similar parts and in which:

FIG. 2 is a schematic view of the optical portion of the apparatus of FIG. 1 depicting the light source, two light baffles, the sample to be analyzed and photoelectric means;

FIG. 5 is a schematic circuit diagram of the apparatus of FIG. 1; and

DESCRIPTION OF THE PREFERRED EMBODIMENT

Referring now more particularly to the drawings, a nephelometer 10 is illustrated for testing bacteria samples to determine whether the samples contain a predetermined bacteria count and hence whether the sample is standardized. Accordingly, the apparatus is referred to as a Standardized Inoculum Reader.

Figure 1:
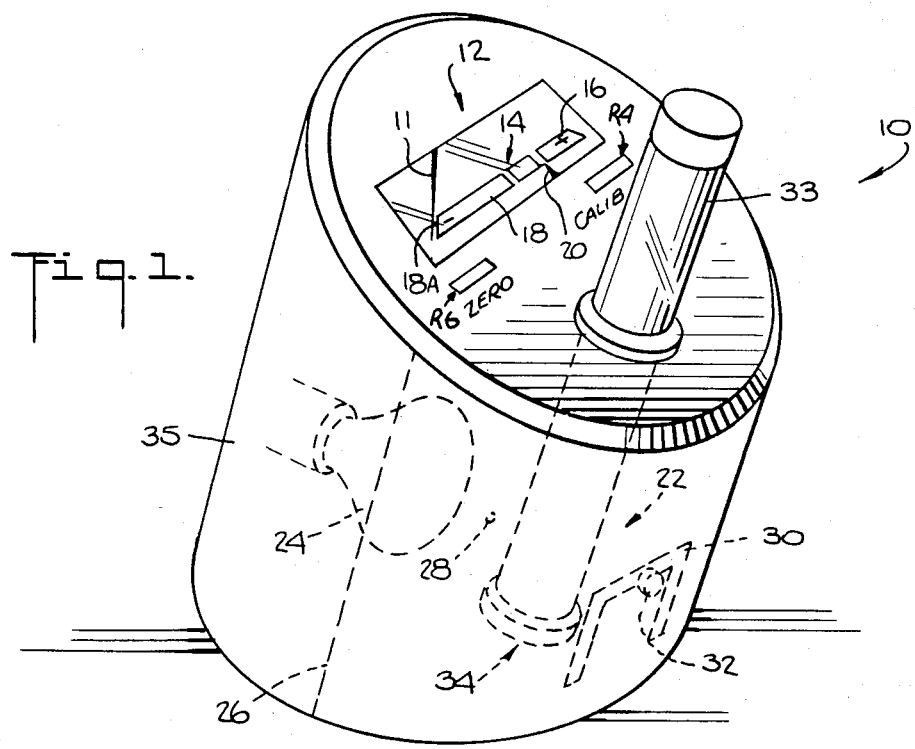
FIG. 1 is a perspective view of the apparatus according to the invention.

To determine whether the bacteria samples contain the standardized concentration utilizing the Standardized Inoculum Reader 10 shown in FIG. 1, the Reader 10 is calibrated using a sample having a McFarland standard concentration so that the indicator 11 of the meter 12 has a reading in the central area 14 of the meter face between the "+" area 16 and the "−" area 18 and superposed with line 20. The McFarland standard concentration is a solution of barium sulphate ($BaSO_4$) particles in a concentration of about $1 \times 10^8$ particles per ml. After the Reader 10 has been calibrated for the McFarland standard concentration, bacteria samples are tested against the McFarland standard concentration. Bacteria samples for which bacteria counts of from about $0.5 \times 10^8$ to about $5 \times 10^8$ per ml are desired when tested in the Reader 10 will give a meter reading in the area 14 corresponding to an actual bacteria count of from about $1 \times 10^8$ per ml to about $2 \times 10^8$ per ml.

Figure 3:
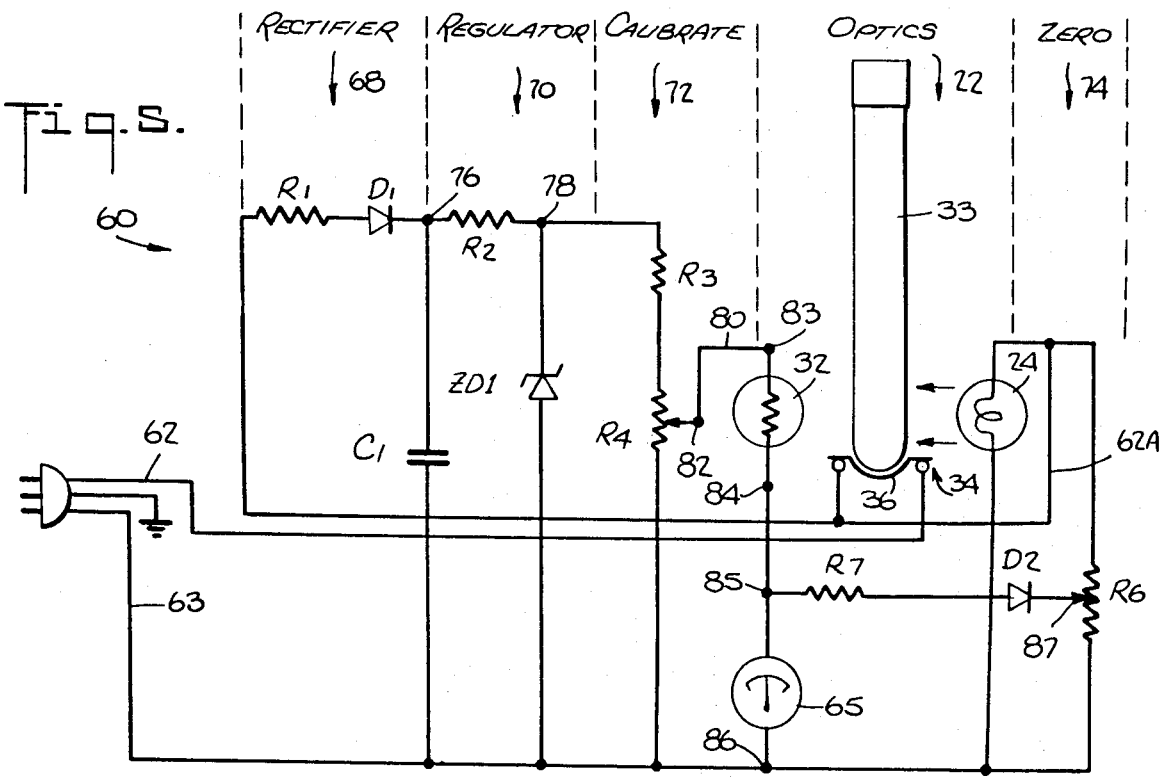
FIG. 3 is a schematic view of the optical portion shown in FIG. 2 taken along lines 3—3 of FIG. 2.

Referring now to FIGS. 1-3, the Standard Inoculum Reader 10 includes an optical section 22 which comprises a lamp 24, an opaque baffle 26 having an orifice 28 therein, another opaque baffle 30 and a photoresistor 32. The bacteria sample to be analyzed is contained in a sample container 33 in the form of a test tube which is inserted into a receptacle 34 to conduct a test. The optical section 22 is enclosed in an opaque housing 35 to prevent stray light from reaching the sample container. The receptacle 34 includes a pressure sensitive switch 36 (FIG. 5) which is engaged by the bottom of the test tube 33 and which controls illumination of the lamp 24. Depressing the container 33 activates the switch to switch the lamp on, and releasing the container, deactivates the switch to switch the lamp off. The lamp 24 projects light towards the opaque baffle 26 about an optical axis 38 (FIG. 2) which passes through the orifice 28 in a diverging beam 39. The baffle 30 and the photoresistor 32 are disposed along the optical axis 38 to one side of the container 33 while the lamp 24 and baffle 26 are disposed to the opposite side of the container 33. The photoresistor 32 is spaced from the receptacle 34. The space 41 (FIG. 4) between a container 33 in the receptacle and the photoresistor is open except for the disposition of the baffle 30 therein.

The diameter of orifice 28 is about two mm while the face of lamp 24 is approximately three cm in diameter. Accordingly, beam 39 diverges as it propagates from orifice 28 through container 33. Orifice 28 is beveled to assist in providing a diverging beam.

The particles suspended in the McFarland standard concentration scatter light from beam 39 as it passes through container 33. For example, light ray 40 of beam 39 is resistor 32. By virtue of baffle 30, light within the region bounded by the imaginary lines 43 and passing through the imaginary region shown at 46, which is transmitted directly (i.e. without scattering) from lamp 24 through container 33 toward photoresistor 32 is prevented from intercepting the latter. Correspondingly, light from beam 39 scattered within that portion of container 33 opposite baffle 30 also will not reach photoresistor 32. Accordingly, photoresistor 32 only detects light scattered by particles suspended in the sample and falling without that portion of container 33 which is not directly opposite baffle 30.

An upper sleeve 45, opaque to light in beam 39, is disposed about the upper portion of container 33 and extends downwardly to a level above the baffle 30. Sleeve 45 serves to minimize errors due to meniscus reflection and scattering, and due to ambient light, and to define the largest detectible scattering angle (measured with respect to optical axis 38) in the upper part of container 33. A lower sleeve 47, also opaque to light in beam 39, is disposed about the lower portion of container 33 and extends upwardly to a level below the baffle 30. Sleeve 47 serves to minimize the effects of bottom focus and scattering, and to define the largest detectible scattering angle in the lower part of container 33. The mean scattering angle is determined principally by the distance of baffle 30 from container 33 and the distance of baffle 30 from photoresistor 32, and is preferably selected to be approximately 45°. By virtue of the characteristic distribution of light intensities over the detectible range of scattering angles, a corona or halo effect illustrated by an imaginary annular region 44, is observable on the surface of container 33.

Figure 4:
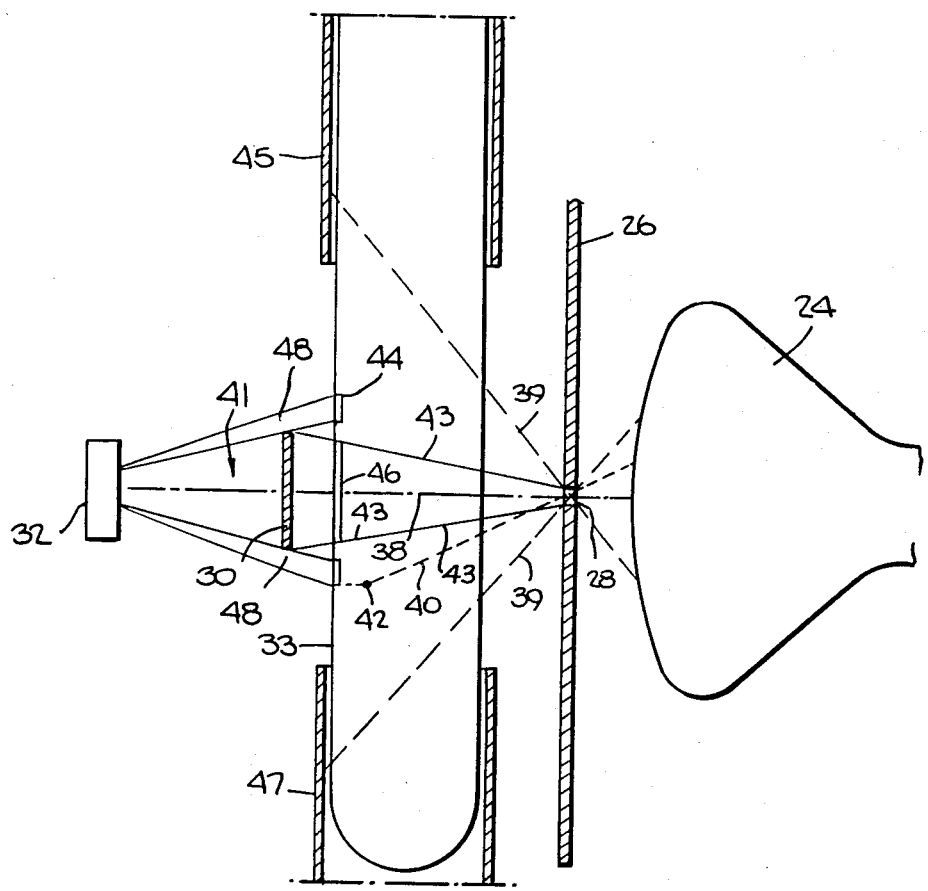
FIG. 4 is an enlarged schematic view of the optical portion shown in FIG. 2 taken along lines 4—4 of FIG. 2.

Baffle 30 which is disposed in space 41 on the optical axis, extends radially thereabout and prevents all light directly transmitted from lamp 24 which passes through the region 46 from reaching the photoresistor 32. Thus, no directly transmitted light is permitted to reach the photoresistor 32. The baffle 30 and the photoresistor 32 are sized and positioned so that light projected from the annular region 44 is permitted to reach the light sensitive area of the photoresistor 32, i.e. parts of the sensitive area of the photoresistor are in the field of view of the halo (FIG. 4). Nothing is disposed in space 41 except baffle 30 and therefore the light from annular region 44 is directly transmitted through space 41 to the parts of the photoresistor in the field of view 48 of the annular region 44. The light in the annular region 44 which thus reaches the photoresistor 42 is a measure of the particle count of the barium sulphate or of bacteria in container 33. The intensity of the light in the annular region 44 is directly proportional to the number of particles or bacteria in the container 33, i.e. the higher the concentration of particles or bacteria, the more light that is reflected to the annular region 44. The conductivity of photoresistor 32 is directly proportional to the intensity of the light which impinges upon its light sensitive surface area.

With particular reference to FIGS. 2 and 3, a generally rectangular baffle 30 is employed with a cylindrical container, such as container 33, to eliminate lensing effects of the curved surface of container 33. That is, light in beam 39 which is refracted at the surface of container 39 but not scattered by particles in the sample will be prevented from reaching photoresistor 32 by baffle 30. By virtue of the rectangular shape of baffle 30, light in the upper region 44A and the lower region 44B of region 44 is permitted to reach photoresistor 32.

Referring now to FIG. 5, the photoresistor 32 is shown connected in a measuring circuit 60. The pressure sensitive switch 36 is in an on/off switch for the apparatus and connects and disconnects AC power to the apparatus and to the circuit 60. Lines 62 and 63 connect AC power to the switch. Depressing container 33 into receptacle 34 activates the pressure sensitive switch 36 to switch power into the circuit 60 and illuminate lamp 24 which is connected between the switched AC power line 62A and the neutral AC line 63. Photoresistor 32 is disposed to receive the light transmitted by lamp 24 and scattered by the McFarland standard concentration or the bacteria sample in container 33 into the annular halo region 44, as described above.

Circuit 60 in addition to Optics Section 22 includes a Rectifier Section 68, a Regulator Section 70, a Calibrate Section 72 and a "Zero" Section 74. The Rectifier Section 68 is connected between the switched AC line 62A and the neutral AC line 63 and comprises resistor R1 connected in series with a rectifier diode D1, and a filter capacitor C1 connected in shunt with the series-connected resistor R1 and diode D1, and the neutral line 63. Rectifier Section 68 operates in conventional fashion to provide half-wave rectified DC at the output 76 of the Rectifier Section. The half-wave rectified DC is fed to the Regulator Section 70 which comprises a limiting resistor R2 connected at one terminal thereof to diode D1, and a zener diode ZD1 connected in shunt to the other terminal of resistor R2 and neutral line 63. The Regulator Section 70 operates in conventional fashion to provide a regulated DC voltage at its output 78 having a value of approximately the zener breakdown voltage of zener diode D1. The regulated DC voltage is fed to series-connected resistors R3 and R4 which are connected across the output 78 of the Regulator Section. Resistor R4 is a potentiometer whose setting determines the DC voltage at the wiper arm 80 of potentiometer R4. Resistors R3 and R4 are connected as a voltage divider to provide a divided DC voltage at point 82. Resistor R4 is adjusted as will be described below to provide a calibrated output reading on meter 65. The wiper arm 80 of the potentiometer R4 is connected to one terminal 83 of the photoresistor 32 and the other terminal 84 of the photoresistor 32 is connected to one terminal 85 of meter 65. The other terminal 86 of meter 65 is connected to the neutral line 63.

The current which flows through meter 65 is determined by the conductivity of photoresistor 32 and the setting of potentiometer R4, and by the Zero Section 74. The Zero Section comprises potentiometer R6 connected across the switched AC line 62A and the neutral AC line 63, a diode D2 connected to the wiper arm 87 of potentiometer R6 and to resistor R7 which is connected in series with diode D2 and terminal 85 of meter 65. Resistor R7 and diode D2 provide a negative half-wave rectified voltage which is coupled to meter 65. The value of the half-wave rectified DC voltage is determined by adjustment of potentiometer R6.

Figure 6:
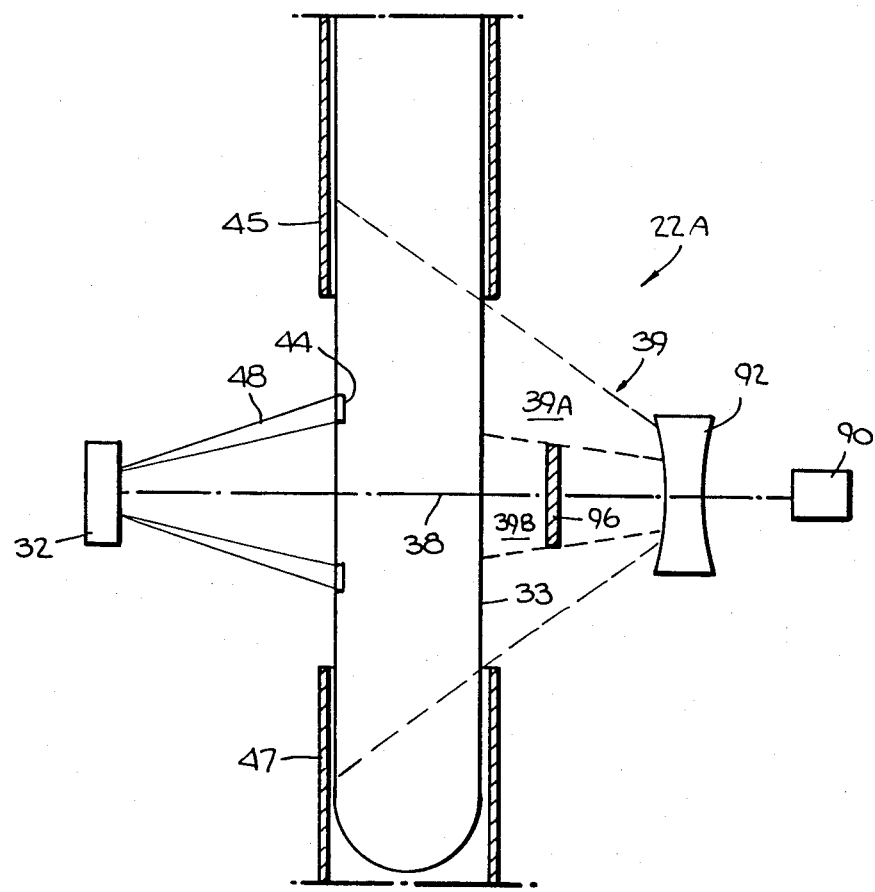
FIG. 6 is an enlarged schematic view, similar to FIG. 2, of another embodiment of the optical portion.

Referring now to FIG. 6, another embodiment of an optical section 22A is illustrated. A lamp 90 and a negative lens 92 cooperate to provide a diverging beam of light 39 which is projected towards the container 33. An opaque baffle 96 is interposed between the lens 92 and the container 33 on the optical axis 38. The baffle 96 is sized and spaced between the container and lens to permit a portion 39A of the diverging beam of light 39 to reach the container. Light 39B propagating towards the container about the axis 38 is blocked by the baffle 96 and prevented from reaching the container 33. The diverging light 39A which enters the sample is scattered in a manner similar to that described for the embodiment of FIGS. 1-4 producing the halo region 44. The light in the halo region 44 is permitted to reach the photoresistor 32, while the light 39B propagating about the about axis 38 is blocked and accordingly does not reach the photoresistor 32. As for the embodiment of FIGS. 1-4, the intensity of the light in the annular region 44 will be directly proportional to the number of particles or bacteria in the container 33.

OPERATION

The Standardized Inoculum Reader 10 is calibrated at the factory or in the field as follows. A container 33 holding a "zero" sample, i.e. a sample having no particles or a negligible number of particles and which will not produce the halo 44, is inserted into receptacle 34 and is depressed to activate the system. Photoresistor 32 receives no light and its conductivity is therefore at a minimum. Potentiometer R6 which is accessible from the exterior of housing 35 (FIG. 1) is adjusted to provide a meter reading which coincides with line 18A at the extreme left of the minus area of the meter face. Line 18A indicates a "zero" particle count. The "zero" sample container is removed and a container 33 holding a McFarland standard concentration sample is inserted in receptacle 34 and depressed to activate the system. Potentiometer R4 (accessible from the exterior of housing 35 (FIG. 1)) is adjusted to provide a meter reading coinciding with line 20 in the central region 14 of the meter. The McFarland standard concentration sample container is removed and the "zero" sample container is reinserted and the potentiometer R6 readjusted to provide the "zero" indication. The "zero" sample container is again removed and the McFarland standard concentration container is again inserted and the potentiometer R4 again adjusted for a meter reading coinciding with line 20. Since there is some interaction between potentiometer R4 and potentiometer R6, the last two steps may be repeated until no further adjustment is necessary.

Standard Inoculum Reader 10 is now factory calibrated to compare bacteria counts to the particle count of a McFarland standard concentration. In use, however, it may be necessary to zero and calibrate the system using "zero" and McFarland standard concentrations and adjusting potentiometers R6 and R4 to insure continued accuracy.

After being calibrated as described above, the Standard Inoculum Reader 10 is used to determine whether bacteria samples have a predetermined bacteria count and hence may be used as standardized samples. These are "go", "no-go" tests. The container 33 containing the bacteria sample to be tested is inserted into the Reader 10 and depressed to activate the pressure sensitive switch 36 to activate the system. The intensity of the light in the halo or annular region 44 is directly proportional to the bacteria count of the sample, i.e. the more intense the light in halo region 44 is, the higher the number of bacteria in the sample. Photoresistor 32 has a conductivity which is directly proportional to the intensity of light received on its light effective surface area and the more conductive that photoresistor 32 is, the more current that is fed to meter 65. Thus, the more intense the light in the annular region 44 is, the more current is supplied to meter 65. Accordingly, higher bacteria counts will read in the right region 16 of the meter while lower bacteria counts will read in the left region 18 of that meter. Thus, if the meter reading is between the "+" and "−" area of the meter, i.e. in the central region 14, then the bacteria sample contains approximately the predetermined number or count of bacteria and can be used as a standardized concentration. If the meter reads in the "−" area 18, then the number or count of bacteria is lower than the predetermined number and if the meter reads in the "+" region 16 to the right of the central region, then the bacteria count of the sample exceeds the predetermined number.

While the baffles 30 and 96 have been shown spaced from the container 33, it is contemplated that they may be placed elsewhere in accordance with the optical geometry of a particular system, for example on a container surface. Additionally, it is contemplated that optical systems other than the lamp 24 and baffle 26, and the lamp 90 and lens 92, may be utilized to provide a diverging beam of light 39.

The advantages of the present invention as well as certain changes and modifications of the disclosed embodiments thereof will be readily apparent to those skilled in the art. It is the applicants' intention to cover by their claims all those changes and modifications which can be made to the embodiment of the invention herein chosen for the purposes of the disclosure without departing from the spirit and scope of the invention.

What is claimed is:

1. Photometric apparatus comprising a source of light for projecting light towards a sample to be analyzed, photoelectric means positioned to receive light projected by the source emerging from the sample and having electrical characteristics dependent upon the light received by the photoelectric means, DC power source means for providing DC power at an output thereof to the photoelectric means, indicator means coupled to the photoelectric means, first adjustment means coupled between the photoelectric means and the DC power source means for adjusting the DC power provided to the photoelectric means, and second adjustment means including rectifier means coupled between a source of AC power and the indicator means for providing DC power at an adjustable level to the indicator means.

2. The photometric apparatus as recited in claim 1, wherein the first adjustment means comprises a resistive voltage divider coupled between the output of the source of DC power and the photoelectric means.

3. The photometric apparatus as recited in claim 2, wherein the photometric means comprises a photoresistor.

4. The photometric apparatus as recited in claim 3, wherein the second adjustment means comprises a resistive voltage divider coupled between the source of AC power and the indicator means.

5. The photometric apparatus as recited in claim 4, wherein the resistive voltage divider of the second adjustment means comprises a potentiometer having its fixed terminal adapted to be connected across the source of AC power and its adjustable terminal coupled to the rectifier means which in turn is coupled to the indicator means.

6. The photometric apparatus as recited in claim 5, wherein the rectifier means comprises a diode connected to provide a negative half-wave rectified voltage to the indicator means and wherein the DC power source means is operative to provide a positive DC voltage to the first adjustment means.

* * * * *